(12) United States Patent
Edwards et al.

(10) Patent No.: US 11,911,771 B2
(45) Date of Patent: Feb. 27, 2024

(54) RETRACTABLE AND HYBRID DIAGNOSTIC TEST DEVICES, KITS AND METHODS

(71) Applicant: LIA DIAGNOSTICS, INC., Philadelphia, PA (US)

(72) Inventors: Bethany Edwards, Harveys Lake, PA (US); Anna Couturier, Philadelphia, PA (US); Jino Lee, Philadelphia, PA (US)

(73) Assignee: LIA DIAGNOSTICS, Inc., Philadelphia, PA (US)

( * ) Notice: Subject to any disclaimer, the term of this patent is extended or adjusted under 35 U.S.C. 154(b) by 229 days.

(21) Appl. No.: 16/769,903

(22) PCT Filed: Dec. 4, 2018

(86) PCT No.: PCT/US2018/063922
§ 371 (c)(1),
(2) Date: Jun. 4, 2020

(87) PCT Pub. No.: WO2019/113118
PCT Pub. Date: Jun. 13, 2019

(65) Prior Publication Data
US 2020/0384476 A1    Dec. 10, 2020

Related U.S. Application Data

(60) Provisional application No. 62/594,484, filed on Dec. 4, 2017.

(51) Int. Cl.
*B01L 9/00*    (2006.01)
*B01L 3/00*    (2006.01)

(52) U.S. Cl.
CPC ............ *B01L 9/52* (2013.01); *B01L 3/5023* (2013.01); *B01L 2300/025* (2013.01); *B01L 2300/0825* (2013.01); *B01L 2300/12* (2013.01)

(58) Field of Classification Search
CPC .... B01L 9/52; B01L 3/5023; B01L 2300/025; B01L 2300/0825; B01L 2300/12; B01L 2300/126; G01N 33/487
See application file for complete search history.

(56) References Cited

U.S. PATENT DOCUMENTS

2004/0060677 A1* 4/2004 Huang ................ C09K 17/52
                                                              162/158
2005/0106750 A1* 5/2005 Tung .................. A61B 10/007
                                                              422/562
(Continued)

FOREIGN PATENT DOCUMENTS

WO      9508761 A1      3/1995
WO     98055859 A1     12/1998
(Continued)

OTHER PUBLICATIONS

Glossary with the definition of "flushability" retrieved from INDA.org using the WayBack Machine: https://web.archive.org/web/20160403042253/http://www.inda.org/wp-content/uploads/2015/04/glossaryfc.pdf (Year: 2016).*

*Primary Examiner* — Matthew D Krcha
*Assistant Examiner* — Sophia Y Lyle
(74) *Attorney, Agent, or Firm* — Rimon PC

(57) ABSTRACT

The present disclosure relates to retractable diagnostic devices, and hybrid diagnostic devices comprised of water-dispersible, flushable, biodegradable, or water-soluble material and non-water-dispersible, non-flushable, or non-water-soluble material.

16 Claims, 4 Drawing Sheets

(56) References Cited

U.S. PATENT DOCUMENTS

| | | | | |
|---|---|---|---|---|
| 2005/0142033 A1* | 6/2005 | Glezer | ............... | B01L 3/5085 |
| | | | | 422/400 |
| 2005/0178515 A1* | 8/2005 | Ryan | ............... | D21H 27/30 |
| | | | | 162/168.3 |
| 2005/0250218 A1* | 11/2005 | Andrelczyk | ......... | B01L 3/5023 |
| | | | | 422/400 |
| 2008/0081341 A1* | 4/2008 | Maher | ............... | G01N 33/558 |
| | | | | 435/7.1 |
| 2008/0286879 A1* | 11/2008 | Lee | ............... | G01N 33/558 |
| | | | | 436/164 |
| 2011/0189786 A1 | 8/2011 | Reches et al. | | |
| 2012/0148458 A1* | 6/2012 | Benson | ............... | B01L 3/5023 |
| | | | | 422/401 |
| 2015/0056687 A1* | 2/2015 | Tyrrell | ............... | B01L 3/5023 |
| | | | | 422/402 |

FOREIGN PATENT DOCUMENTS

| | | | |
|---|---|---|---|
| WO | 2011018618 A2 | 2/2011 | |
| WO | 2015175301 A8 | 12/2016 | |
| WO | 2017024271 A1 | 2/2017 | |
| WO | WO-2017103875 A1 * | 6/2017 | |

* cited by examiner

FIG. 6A      FIG. 6B
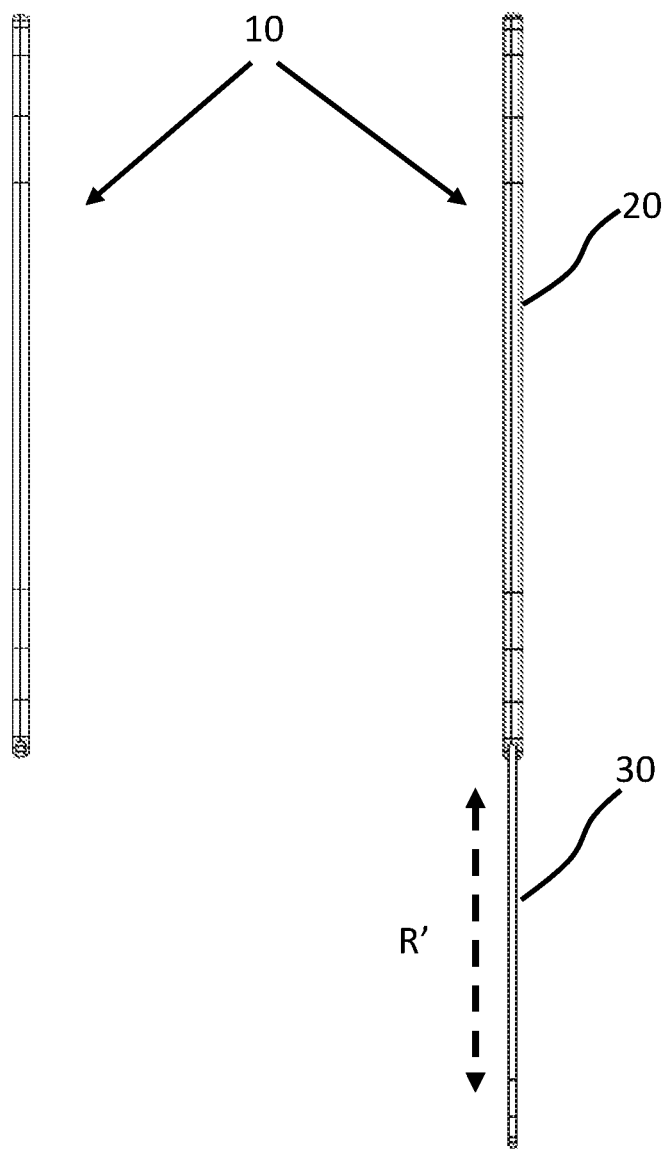
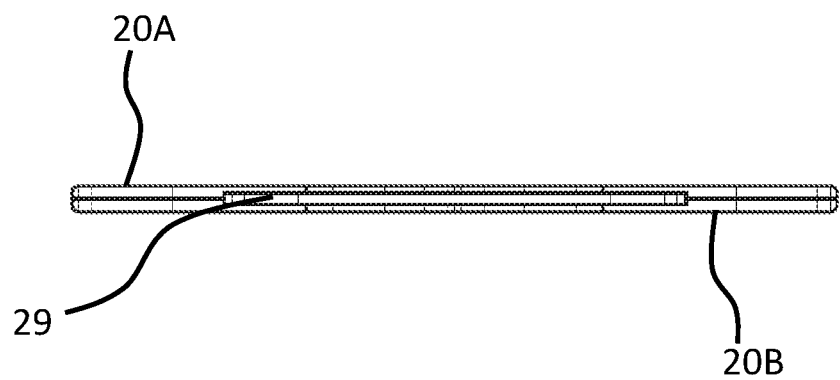
FIG. 6C

RETRACTABLE AND HYBRID DIAGNOSTIC TEST DEVICES, KITS AND METHODS

CROSS-REFERENCE TO RELATED APPLICATIONS

This application is a United States national stage entry of International Application serial no. PCT/US2018/063922 filed Dec. 4, 2018, which claims priority to U.S. Provisional Patent Application Ser. No. 62/594,484 filed Dec. 4, 2017. The contents of these applications are incorporated herein by reference in their entirety as if set forth verbatim.

BACKGROUND

The field of rapid diagnostic testing has developed to permit the detection of analytes in a variety of sample types. The use of polyclonal antibodies was followed by the use of monoclonal antibodies to generate assays with high specificity for a number of analytes, including hormones, cells, drugs and their metabolites, as well as the antigens of infectious agents. The visible signal generated by enzyme-catalyzed reactions or by the accumulation of a visible signal at the level of a test line has also resulted in rapid development of highly sensitive results. Many of the rapid immunoassay-based tests include a solid housing encasing a test strip.

Existing devices typically comprise multiple parts: a rigid plastic structure to serve as a support for the device, and a nitrocellulose-based testing strip which carries out the test itself. Such devices use rigid plastic body structures, an imprecise specimen collection method (sometimes requiring counting from the user), singular abstract readout per testing strip (in non-electronic devices), and landfill disposal. Nitrocellulose membranes are synthetic and non-water dispersible and not soluble. Urine-based diagnostics usually fall into the categories of midstream (device is held in flowing stream of fluid), dip (device is held in stationary fluid sample), and cassette (dropper is used to add fluid sample).

The solutions presented herein address these and other needs in the art.

SUMMARY

In certain frequent embodiments, a water dispersible, flushable, biodegradable, and/or compostable diagnostic assay is provided comprised completely of water dispersible, flushable, biodegradable, and/or compostable materials having an outer housing and an inner translatable diagnostic insert that can be moved between retracted and extended positions.

In certain embodiments, a diagnostic device is provided for identifying or quantifying an analyte of interest in a biological sample, comprising a housing; and a diagnostic insert, where the housing is adapted to receive the diagnostic insert in a translatable or detachable configuration, and the housing or the diagnostic insert are comprised of at least one water-dispersible, flushable, biodegradable, or water-soluble material. In often included embodiments, the housing and the diagnostic insert are comprised of water-dispersible, flushable, or water-soluble material. Also, in often included embodiments, the housing or the diagnostic insert are comprised of water-dispersible, flushable, or water-soluble material. In certain included embodiments the housing is adapted to receive the diagnostic insert in a translatable configuration, wherein the translatable configuration permits movement of the diagnostic insert between a retracted position and an extended position. Often in such embodiments, the retracted position situates the majority or the entirety of the diagnostic insert within the housing. In certain included embodiments the device the device further comprises a test strip, wherein the diagnostic insert or the housing is adapted to removably receive the test strip. Often, the test strip comprises a non-water-dispersible, non-flushable, or non-water-soluble material, and is frequently comprised at least partially of nitrocellulose, or contains functional aspects of the strip that comprise nitrocellulose. Alternatively, the test strip may be comprised or consist of non-nitrocellulose material such as non-nitrocellulose test strips described herein. Such test strips may comprise a water-dispersible, flushable, biodegradable or water-soluble material. In often included embodiments, the housing comprises a biodegradable material or a non-water-dispersible, non-flushable, or non-water-soluble material. In certain embodiments described herein the diagnostic described above and below features a housing that is adapted to receive the diagnostic insert in a detachable configuration. Often the diagnostic device features a flushable housing and/or a flushable diagnostic insert.

The devices of the present disclosure may be adapted to provide diagnostic utility in connection with the identification or quantification of any particular analyte, often dubbed an analyte of interest. Proprietary or specific chemistries for specific analytes known in the art are contemplated for such identification or quantification. Such devices may be adapted to detect or quantify an analyte of interest comprising a toxin, an organic compound, a protein, a peptide, a microorganism, a bacteria, a virus, an amino acid, a nucleic acid, a carbohydrate, a hormone, a steroid, a vitamin, a drug, a pollutant, a pesticide, an antigenic substance, a hapten, an antibody, and/or a metabolite of or an antibody to any of the foregoing.

In certain embodiments, a diagnostic device for identifying or quantifying an analyte of interest in a biological sample is provided, featuring a housing and a test strip, where the housing is adapted to removably receive the test strip, and where the housing is comprised of at least one water-dispersible, flushable, biodegradable, or water-soluble material. Often, the at least one water-dispersible, flushable, biodegradable, or water-soluble material comprises a matrix material. Also often, the housing and/or the test strip is/are flushable. In certain selected embodiments, the test strip comprises a non-water-dispersible, non-flushable, or non-water-soluble material. Frequently in such embodiments, the test strip is comprised at least partially of nitrocellulose. Alternatively, the test strip may be comprised or consists of non-nitrocellulose material.

These and other embodiments, features, and advantages will become apparent to those skilled in the art when taken with reference to the following more detailed description of various exemplary embodiments of the present disclosure in conjunction with the accompanying drawings.

BRIEF DESCRIPTION OF THE DRAWINGS

The skilled person in the art will understand that the drawings, described below, are for illustration purposes only.

FIG. 6A depicts a side view of an exemplary device embodiment with the diagnostic insert in a retracted position.

FIG. 6B depicts a side view of an exemplary device embodiment with the diagnostic insert in an extended position.

FIG. 6C depicts a front side view of an exemplary device embodiment.

DETAILED DESCRIPTION OF THE VARIOUS EMBODIMENTS

Figure 1:
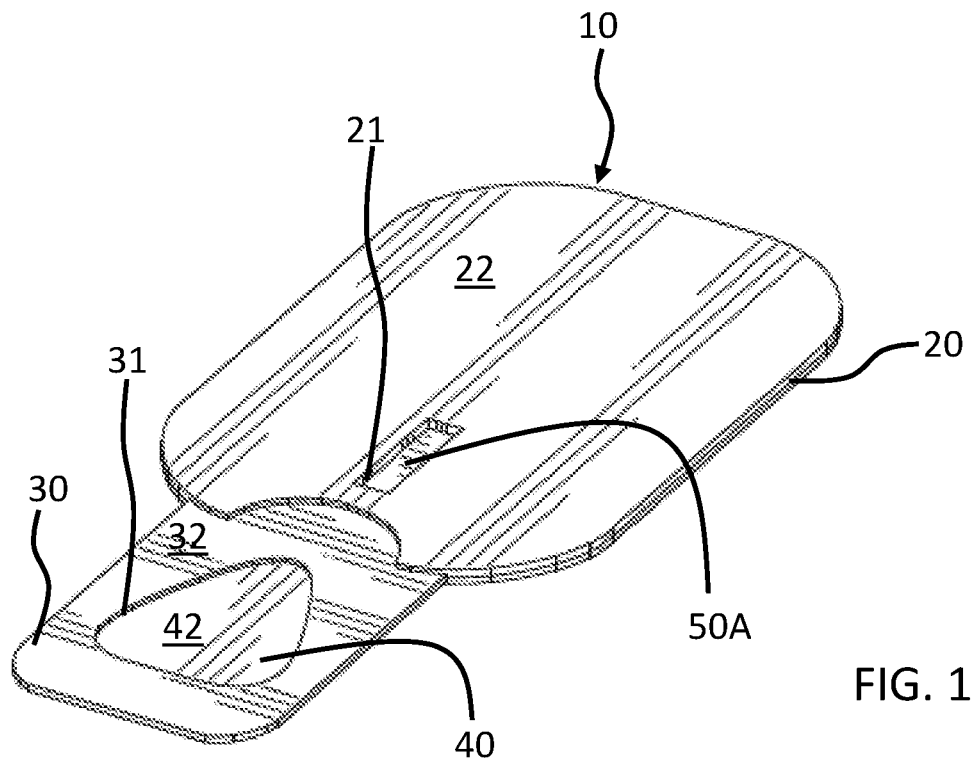
FIG. 1 depicts an upper perspective view of an exemplary device embodiment with the diagnostic insert in an extended position.

For clarity of disclosure, and not by way of limitation, the detailed description of the various embodiments is divided into certain subsections that follow.

Unless defined otherwise, all technical and scientific terms used herein have the same meaning as is commonly understood by one of ordinary skill in the art to which this invention belongs. All patents, applications, published applications and other publications referred to herein are incorporated by reference in their entirety. If a definition set forth in this section is contrary to or otherwise inconsistent with a definition set forth in the patents, applications, published applications and other publications that are herein incorporated by reference, the definition set forth in this section prevails over the definition that is incorporated herein by reference.

As used herein, "a" or "an" means "at least one" or "one or more."

As used herein, the term "and/or" may mean "and," it may mean "or," it may mean "exclusive-or," it may mean "one," it may mean "some, but not all," it may mean "neither," and/or it may mean "both."

As used herein, the term "dispersible" means that the fibers or chunks of a material are capable of debonding or separating, resulting in the material breaking down into smaller pieces than the original sheet. Debonding is generally a physical change of scattering or separation, as compared to a state change, such as dissolving, wherein the material goes into solution, e.g., a water-soluble polymer dissolving in water. For clarity, a material may be dispersible when broken down into smaller clumps of the larger material without fibers dispersing.

As used herein, the term "soluble" has a conventional meaning. In other words, "soluble" refers to the ability of a specified material to dissolve in another substance such as water, a fluid sample, or another fluid.

As used herein, the term "sample" refers to anything which may contain an analyte for which an analyte assay is desired. The sample may be a biological sample, such as a biological fluid sample or a biological tissue sample. Examples of biological fluids include urine, blood, plasma, serum, saliva, semen, stool, sputum, cerebral spinal fluid, tears, mucus, amniotic fluid or the like. Biological tissues comprise an aggregate of cells, usually of a particular kind together with their intercellular substance that form one of the structural materials of a human, animal, plant, bacterial, fungal or viral structure, including connective, epithelium, muscle and nerve tissues. Examples of biological tissues also include organs, tumors, lymph nodes, arteries and individual cell(s).

"Fluid sample" refers to a material suspected of containing the analyte(s) of interest, which material has sufficient fluidity to flow through an immunoassay device in accordance herewith. The fluid sample can be used as obtained directly from the source or following a pretreatment so as to modify its character. Such samples can include human, animal or man-made samples. The sample can be prepared in any convenient medium which does not interfere with the assay. Typically, the sample is an aqueous solution or biological fluid as described in more detail below.

The fluid sample can be derived from any source, such as a physiological fluid, including blood, serum, plasma, saliva, sputum, ocular lens fluid, sweat, urine, milk, ascites fluid, mucous, synovial fluid, peritoneal fluid, transdermal exudates, pharyngeal exudates, bronchoalveolar lavage, tracheal aspirations, cerebrospinal fluid, semen, cervical mucus, vaginal or urethral secretions, amniotic fluid, and the like. Herein, fluid homogenates of cellular tissues such as, for example, hair, skin and nail scrapings, meat extracts and skins of fruits and nuts are also considered biological fluids. Pretreatment may involve preparing plasma from blood, diluting viscous fluids, and the like. Methods of treatment can involve filtration, distillation, separation, concentration, inactivation of interfering components, and the addition of reagents. Besides physiological fluids, other samples can be used such as water, food products, soil extracts, and the like for the performance of industrial, environmental, or food production assays as well as diagnostic assays. In addition, a solid material suspected of containing the analyte can be used as the test sample once it is modified to form a liquid medium or to release the analyte. The selection and pretreatment of biological, industrial, and environmental samples prior to testing is well known in the art and need not be described further.

"Analyte" refers to the compound or composition to be detected or measured and which has at least one epitope or binding site. The analyte can be any substance for which there exists a naturally occurring analyte specific binding member or for which an analyte-specific binding member can be prepared. e.g., carbohydrate and lectin, hormone and receptor, complementary nucleic acids, and the like. Further, possible analytes include virtually any compound, composition, aggregation, or other substance which may be immunologically detected. That is, the analyte, or portion thereof, will be antigenic or haptenic having at least one determinant site, or will be a member of a naturally occurring binding pair.

Analytes include, but are not limited to, toxins, organic compounds, proteins, peptides, microorganisms, bacteria, viruses, amino acids, nucleic acids, carbohydrates, hormones, steroids, vitamins, drugs (including those administered for therapeutic purposes as well as those administered for illicit purposes), pollutants, pesticides, and metabolites of or antibodies to any of the above substances. The term analyte also includes any antigenic substances, haptens, antibodies, macromolecules, and combinations thereof. A non-exhaustive list of exemplary analytes is set forth in U.S. Pat. No. 4,366,241, at column 19, line 7 through column 26, line 42, the disclosure of which is incorporated herein by reference. Further descriptions and listings of representative analytes are found in U.S. Pat. Nos. 4,299,916; 4,275,149; and 4,806,311, all incorporated herein by reference.

As used herein, the phrase "fibrous nonwoven composite structure" refers to a structure of individual fibers or filaments with or without particulates which are interlaid, but not in an identifiable repeating manner. Nonwoven structures such as, for example, fibrous nonwoven webs have been formed in the past, by a variety of processes known to those skilled in the art including, for example, meltblowing and meltspinning processes, spunbonding processes, bonded carded web processes, hydroentangling, pressing, electrospinning, and the like. Such structure is often referred to generally herein as "non-woven" or "non-woven matrix."

As used herein, the phrase "matrix material" includes water-soluble, water dispersible, biodegradable, compostable, and/or flushable material. The matrix material may comprise a nonwoven structure, a porous structure, semi-porous structure, gel, a solid, a semi-solid, or other structure. the presently described devices utilize a non-synthetic matrix material as comprising the test region. As used herein, the term "matrix material" (including non-synthetic matrix material, water dispersible or soluble matrix material, water dispersible matrix sandwich material, etc.) excludes nitrocellulose and nitrocellulose material.

As used herein, the phrase "water dispersible" refers to a material (often nonwoven and fibrous) that, when placed in an aqueous environment will (over time) break apart into smaller pieces or fibers. Once the structure is broken apart and dispersed, it is processable in recycling processes, for example, septic and municipal sewage treatment systems. If desired, the fibrous nonwoven structures can be made more water-dispersible or the dispersion can be quickened. The actual amount of time for dispersion can vary and be predetermined based on the intended use profile. A water dispersible material may also be biodegradable.

As used herein, "biodegradable" refers to a material that is capable of being decomposed by bacteria or other living organisms, natural processes, or other biological agents or means. A biodegradable material may also be water dispersible.

As used herein, "flushable" refers to materials that pass the flushablity guidelines of INDA and/or EDANA, for example, as set forth in "Guidelines for Assessing the Flushability of Disposable Nonwoven Products," Third Edition, August 2013 (or current edition/guidelines), INDA and EDANA, or another current industry accepted flushability standard, guideline, recommendation, requirement, or objective.

As used herein, "absorbent" refers to the capacity or tendency to absorb a fluid. Though not wishing to be bound by any particular theory, absorbent materials have a tendency to resist wicking of fluids therethrough.

As used herein, "rigid" refers to an ability to hold form without deformation, bending, creasing or otherwise being forced out of shape. A rigid material may be formable such that can be manipulated to form a shape (e.g., when wetted) and this shape is resistant to deformation under certain conditions (e.g., when dried). A rigid material may have some low degree of flexibility over a given length, depending on the applied force. A rigid material may have varying degrees of rigidity. A water dispersible matrix described herein is often a rigid water dispersible matrix.

Other features and advantages of the disclosure will be apparent from the following description and referenced drawings. The present innovations are often further described by exemplary embodiments. The examples are provided solely to illustrate the innovations by reference to specific embodiments. The drawings, which are not necessarily to scale, depict selected embodiments and are not intended to limit the scope of the present disclosure. These exemplifications, while illustrating certain specific aspects of the innovations, do not portray the limitations or circumscribe the scope of the disclosed innovations. The detailed description illustrates by way of example, and is not intended to limit the scope of the present disclosure.

The water dispersible or soluble matrix materials contemplated herein provide, for example, a seamless and environmentally sustainable manufacturing process and use protocol. In particular, in frequent embodiments, a water dispersible or soluble matrix material is utilized to constitute multiple components/aspects of the contemplated devices.

One exemplary material contemplated herein as a water dispersible matrix is a nonwoven fabric material called HYDRASPUN®, or its related products. Though not wishing to be bound by any particular theory of operation, characteristics of this material that are utilized in the presently contemplated methods and devices are an increased resistance to water-dispersion. In other words, this material is and can be characterized as absorbent. In certain embodiments, the nonwoven fabric material comprises water content of less than about 10% by weight. In certain embodiments, the water dispersible or soluble matrix material comprises a dry tri-layered material having an internal layer of, for example, cellulose pulp fibers, an upper layer of said continuous filaments of a water-soluble or water-dispersible polymer and a lower layer of said continuous filaments of a water-soluble or water-dispersible polymer. Other water dispersible or soluble materials are contemplated and described, for example, other cellulose based non-wovens, and materials described in U.S. Pat. Nos. 4,309,469, 4,419, 403, 5,952,251, and/or 8,668,808. SOFTFLUSH® (Jacob Holm & Sons AG) and NBOND® (Hangzhou Nbond Nonwoven Co., Ltd. Corp.) are additional examples of water dispersible and/or biodegradable materials, including matrix materials.

As used herein, the term "matrix material" (including non-synthetic matrix material, water dispersible or soluble matrix material, water dispersible matrix sandwich material, etc.) excludes nitrocellulose and nitrocellulose material. Most frequently, this matrix material comprises a flushable, water dispersible, biodegradable, and/or soluble matrix material such as a nonwoven web material. The term "matrix material" is also intended to refer to the material regardless of whether it has been treated with a coating or lamination.

As noted, the flushable or water dispersible nonwoven materials contemplated herein for use as assay devices or device components, including housing or insert components, are generally absorbent materials. Moreover, such materials also often lack sufficient rigidity to withstand typical use conditions (e.g., using as a mid-stream device) without having to orient them in a specific manner, often using a support. Conversely, when such materials are supported with other materials (e.g., sandwiched materials, laminates, or coatings) those materials often interfere with the ability of the device to become wetted sufficient to initiate dispersion. For example, the materials may cause the device to float on the water surface for an extended time due to the added time it takes for water to pass into or across the laminate or coating to initiate dispersion. The drawbacks to such delayed dispersion are significant, including the inability to pass flushability standards.

Non-water dispersible and non-water-soluble materials are also contemplated herein for use in the presently described devices. For example, in certain embodiments, the Non-water dispersible and non-water-soluble material is a plastic. Such a plastic may be comprised of a polymer that is biodegradable. Also, such a plastic may be comprised of a polymer that is not biodegradable.

Figure 2:
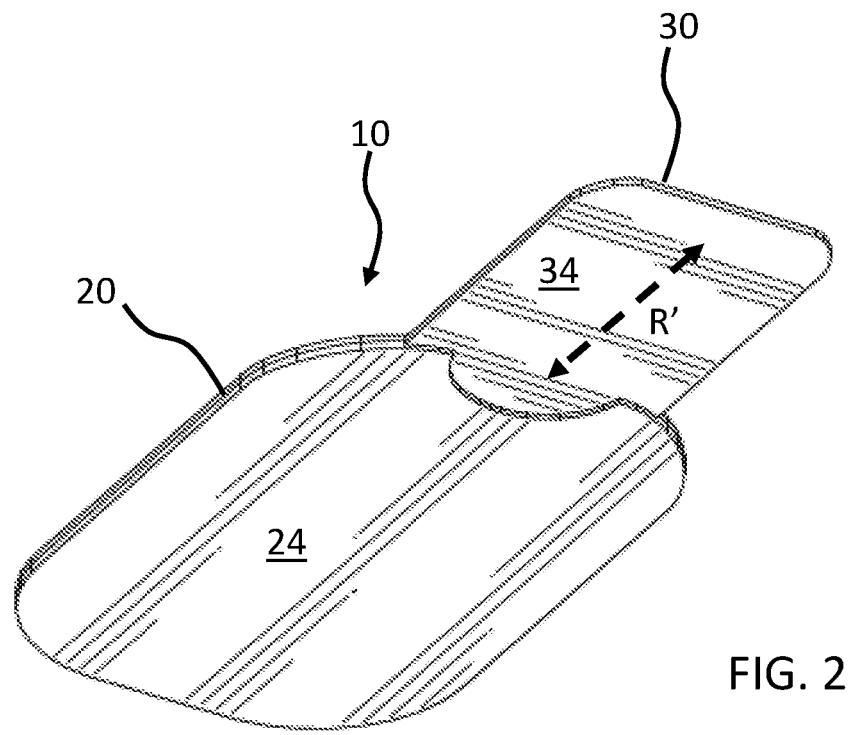
FIG. 2 depicts a lower perspective view of an exemplary device embodiment with the diagnostic insert in an extended position.

Referring to FIGS. 1 and 2, an exemplary device 10 is depicted having an outer housing 20 with top 22 and bottom 24 surfaces, and a fully extended diagnostic insert 30. A window 21 is provided though the surface 22 of the in the outer housing that provides optical access to the diagnostic insert 30 at a position of an assay result or where an assay result may be visible at area 50A. Often the window 21 is protected or covered by a transparent material. This material protecting or covering the window 21 is most frequently light translucent such that a user of the device can see through the material to view a test result. Alternatively, the material is at least partially translucent and must be opened or removed for a user to view a test result. The diagnostic insert 30 includes top 32 and bottom 34 surfaces, and an opening 31 in surface 32 for a sample pad 40 having a sample application surface 42. As exemplified in FIG. 2, diagnostic insert 30 is moveable along direction R' between extended and retracted positions.

Figure 3:
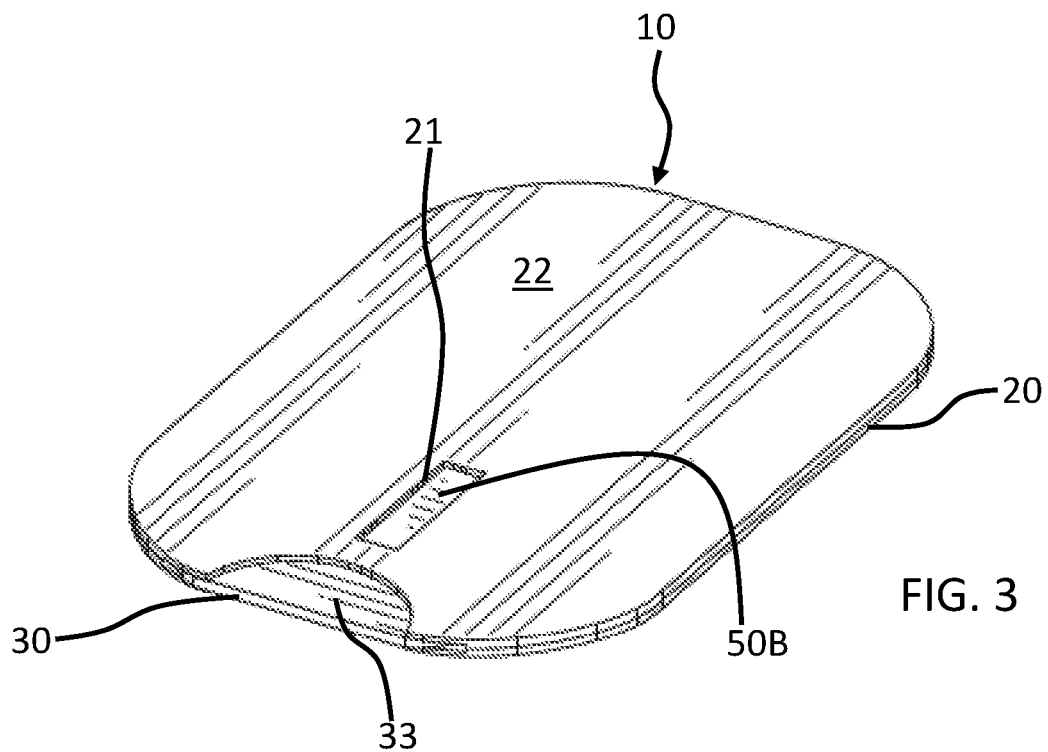
FIG. 3 depicts an upper perspective view of an exemplary device embodiment with the diagnostic insert in a retracted position.
Figure 4:
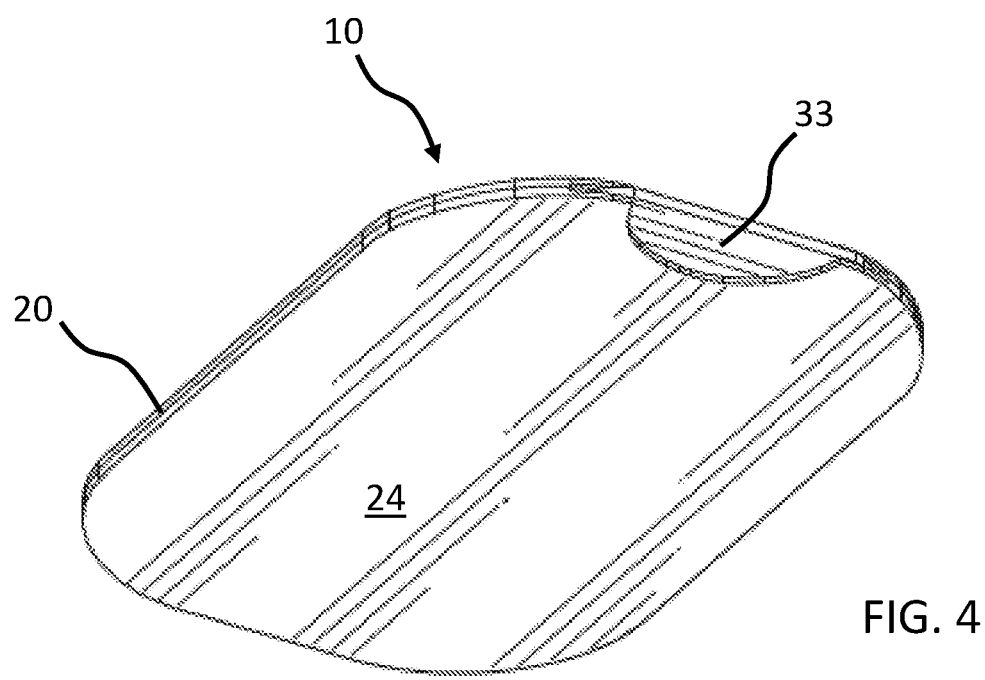
FIG. 4 depicts a lower perspective view of an exemplary device embodiment with the diagnostic insert in a retracted position.

Referring to FIGS. 3 and 4, an exemplary device 10 is depicted having an outer housing 20 with top 22 and bottom 24 surfaces, and a fully retracted diagnostic insert 30. A window 21 is provided though the surface 22 of the in the outer housing that is optionally closed or blocked, or provides optical and/or fluid access to the diagnostic insert 30 at a position 50B. Position 50B may be or comprise the sample pad or a portion thereof, or another aspect of the diagnostic insert 30. In embodiments where position 50B comprises the sample pad 40, the device may optionally be adapted to permit a fluid sample to be applied to the sample pad 40 when the diagnostic insert is in a retracted position. The diagnostic insert 30 includes top 32 and bottom 34 surfaces and tab 33. Tab 33 is optionally a distinct component of diagnostic insert 30 provided to be pulled/pushed to translate the diagnostic insert between retracted and extended positions along direction R'. Tab 33 may also be an indistinct aspect of the diagnostic insert that may be pulled/pushed to translate the diagnostic insert between retracted and extended positions along direction R'.

Figure 5:
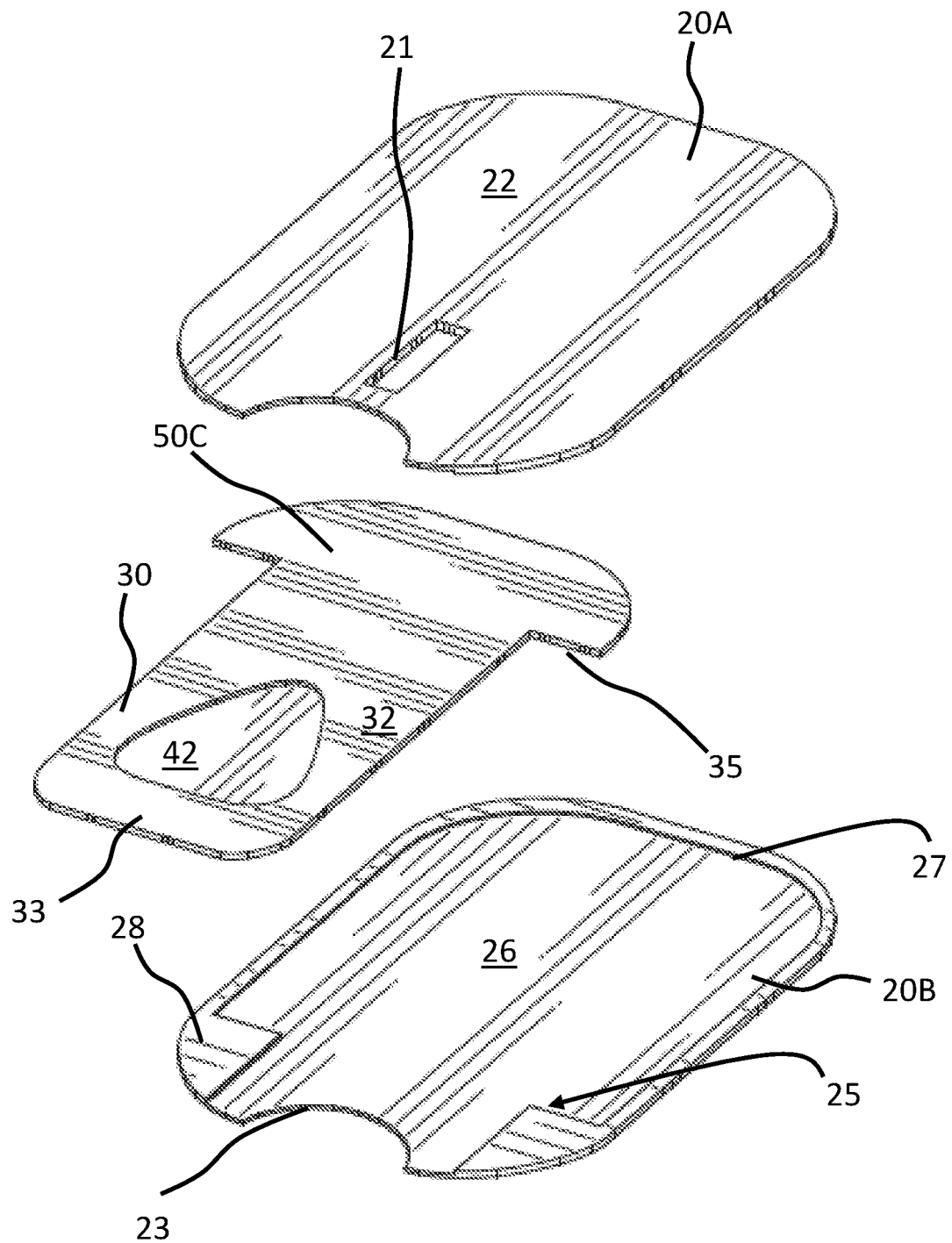
FIG. 5 depicts an upper perspective view of an exploded exemplary device embodiment.

Referring to FIG. 5, an exemplary device 10 is depicted in an exploded state. Outer housing 20 in this Figure shows an exemplary housing top 20A and housing bottom 20B. Outer housing 20 includes a diagnostic insert area 26. This area is depicted in the housing bottom 20B, but may alternatively be located in the housing top 20A, or formed between the housing top 20A and 20B through the presence of a rim 28. Rim is depicted in FIG. 5 as a partial circumferential rim having various physical attributes that are complementary to the shape and dimensions of the diagnostic insert 30, including inner rim wall surface 27 having stop surface 25. Stop surface 25 adapted to physically complement stop portion 35 of the diagnostic insert such that when stop portion 35 contacts stop surface 25, the diagnostic insert 30 is positioned in a fully extended position along direction R'. Stop surface 25 is adapted to prohibit further extension of diagnostic insert 30 from outer housing 20. Diagnostic insert area 26 is depicted having a raised diagnostic insert area 26 is adapted to be capable of housing up to the entire diagnostic insert 30 when in a retracted position. Often, diagnostic insert area 26 includes a gap 23 formed in one or both of the housing top 20A and/or housing bottom 20B that exposes tab 33 (depicted in FIGS. 3 and 4) when the diagnostic insert is partially or fully retracted.

Depicted as a raised ridge, rim 28 of the housing bottom 20B may serve as a location for adhesive application to adhere housing top 20A and housing bottom 20B or the use of other manners of connecting the housing top 20A and housing bottom 20B. This depiction is merely exemplary. Stapleless stapling, integrated male/female connections, latches, snaps, electrostatic connections, or other manners of connecting housing top 20A and housing bottom 20B are contemplated.

Depicted as portion 50C, the diagnostic insert includes what is referred to herein as a downstream portion in top surface 32 of the diagnostic insert or integrated in the top surface 32 of the diagnostic insert similar to sample pad 40 by way or an opening (not depicted). Portion 50C often comprises an area where a visual indication of an assay result is provided. Portion 50C may be the same area or comprise area 50A of FIG. 1. One or more test and/or control line(s) may be provided in area 50A or 50C. Area 50C may optionally include an absorbent area useful to accept fluid that has passed through one or more test and/or control line(s). In certain embodiments, the sample pad is part of a test strip that is integrated into the diagnostic insert 30. In other embodiments, the diagnostic insert 30 comprises the test strip. Area 50C is most frequently adapted such that when the diagnostic insert 30 is fully extended, a viewing window including a test/control area in or comprising area 50C is visible through window 21 in the outer housing 20.

FIGS. 6A and 6B depict side views of an exemplary device, with the diagnostic insert 30 in retracted (6A) and extended (6B) positions. FIG. 6C depicts a front side view of an exemplary device, depicting opening 29 between housing top 20A and housing bottom 20B. Opening 29 is provided to permit the diagnostic insert 30 extend and/or retract along direction R'.

Each of the exemplary devices depicted in FIGS. 1, 2, 3, 4, 5, 6A, 6B, and 6C are most frequently comprised of a water dispersible matrix material or water-soluble material. Often, the same water dispersible matrix material or water-soluble material is used to form each described and/or depicted feature or component of the exemplary devices depicted in FIGS. 1, 2, 3, 4, 5, 6A, 6B, and 6C. In certain embodiments, the exemplary devices depicted in FIGS. 1, 2, 3, 4, 5, 6A, 6B, and 6C are comprised of a combination of water dispersible matrix material and water-soluble material. In certain embodiments, the exemplary devices depicted in FIGS. 1, 2, 3, 4, 5, 6A, 6B, and 6C are comprised of a combination of water dispersible matrix material and/or water-soluble material, and non-water dispersible material such as a plastic polymer or nitrocellulose.

The diagnostic insert is generally provided with sufficient rigidity to withstand movement between an extended and a retracted position within outer housing. Most frequently, the diagnostic insert 30 is comprised of matrix material contemplated herein. The diagnostic insert is also provided in certain embodiments with a diagnostic insert area 26 adapted to accept a traditional test strip such as a nitrocellulose test strip to provide a hybrid device. In certain embodiments the test strip is not comprised of nitrocellulose, e.g., a non-nitrocellulose test strip such as but not limited to exemplary test strips of U.S. Pat. Nos. 9,606,116, 10,045,694, and U.S. Patent Application Publication No. 20180224436, each of which is incorporated herein by reference. As such, an exemplary device of the present disclosure may comprise a hybrid device comprised partially of water-soluble or water dispersible material and partially of material that is not water dispersible and/or not water-soluble.

With further reference to FIGS. 1-6, in certain embodiments the housing 20 and diagnostic insert 30 are comprised of a hybrid of materials, at least one being water dispersible or water-soluble, and at least one being not water dispersible, not flushable, and not water-soluble (e.g., plastic, metal, etc.). For example, in certain embodiments the housing 20 is comprised at least partially of a material that is not water dispersible, not flushable, and not water-soluble, and the diagnostic insert 30 is comprised at least partially of a material that is water dispersible, flushable, biodegradable, and/or water-soluble. In such embodiments, often the housing 20 is comprised of a material that is not water dispersible, not flushable, and not water-soluble such as a plastic polymer or nitrocellulose, and often the diagnostic insert 30 is comprised of a material that is water dispersible, flushable, biodegradable, and/or water-soluble such as a water dispersible matrix material.

In other embodiments the housing 20 is comprised at least partially of a material that is water dispersible, flushable, biodegradable, and/or water-soluble, and the diagnostic insert 30 is comprised at least partially of a material that is not water dispersible, not flushable, and/or not water-soluble (e.g., plastic, metal, etc.). In such embodiments, often the housing 20 is comprised of a material that is water dispersible, flushable, and/or water-soluble such as a water dispersible matrix material, and often the diagnostic insert 30 is comprised of a material that is not water dispersible, not flushable, and not water-soluble such as a plastic polymer, a metal or metal alloy, a biodegradable material, or nitrocellulose. In other related embodiments, the housing 20 and the diagnostic insert 30 are comprised at least partially of a material that is water dispersible, flushable, biodegradable, and/or water-soluble, and the diagnostic insert 30 is adapted to hold, house, support, contact, guide, attach to, secure, or be in communication (e.g., data, fluid, physical, etc.) with, a material that is not water dispersible, not flushable, and/or not water-soluble (e.g., plastic, metal, nitrocellulose, etc.). For example, in certain embodiments, the device housing and insert are comprised of a water dispersible material or flushable material such as a water dispersible matrix, and the insert contains or holds a lateral flow test strip such as a traditional nitrocellulose test strip or a test strip comprised of, at least partially, nitrocellulose. Alternatively, the lateral flow test strip may comprise a non-nitrocellulose test strip.

In certain embodiments the housing 20 is comprised at least partially of a material that is not water dispersible, not flushable, and not water-soluble, and the diagnostic insert 30 is comprised at least partially of a material that is not water dispersible, not flushable, and not water-soluble (e.g., plastic, metal, a biodegradable material, nitrocellulose, etc.). In such embodiments, the diagnostic insert is adapted to hold, house, support, contact, guide, attach to, secure, or be in communication (e.g., data, fluid, physical, etc.) with, a diagnostic assay comprising a material that is water dispersible, flushable, biodegradable, and/or water-soluble. In other embodiments, the housing is adapted to hold, house, support, contact, guide, attach to, secure, or be in communication (e.g., data, fluid, physical, etc.) with, a material that is water dispersible, flushable, and/or water-soluble. In certain related embodiments the material that is water dispersible, flushable, biodegradable, and/or water-soluble may be provided in communication with an electrode, biosensor, electrochemically active material, coating or reagent, or other material capable of electronic transfer or transmit a charge or data between the device and another aspect or device adapted to receive, capture, measure, perform a calculation with, or display the charge or data or information obtained from the charge or data. A biosensor such as a biodegradable biosensor, or a component thereof, may comprise the diagnostic insert or test strip of certain embodiments described herein.

While not specifically depicted, in certain embodiments the diagnostic insert is configured in a manner that is attached yet detachable, attachable and/or otherwise detachable or removable from the housing. Often in such embodiments detachability or removability of the diagnostic insert is provided without altering the integrity of the housing. In certain other embodiments, including related embodiments, the diagnostic insert consists of or comprises a test strip such as a nitrocellulose test strip, a diagnostic dipstick, or a non-nitrocellulose test strip. Thus, the housing may be adapted such that it can accept a means for conducting a diagnostic assay, and such means may comprise a material that is or is not water dispersible, flushable, biodegradable, and/or water-soluble. In any event, in such hybrid devices including other hybrid devices described herein, the hybrid device comprises at least one water dispersible, flushable, biodegradable, and/or water-soluble material.

In certain embodiments, the diagnostic insert comprises a replaceable/removable component of the device and can be comprised, consist essentially, or consist, of at least one water dispersible, flushable, biodegradable, and/or water-soluble material. Alternatively, in certain embodiments, the diagnostic insert comprises a replaceable/removable component of the device and can be comprised, consist essentially, or consist, of at least one non-water dispersible, non-flushable, and/or non-water-soluble material. In such embodiments, a kit may be provided that comprises a housing in addition to one or more diagnostic inserts, including a plurality of diagnostic inserts. Often in such embodiments, the housing is comprised of at least one water dispersible, flushable, biodegradable, and/or water-soluble material and the diagnostic insert optionally comprises at least one water dispersible, flushable, biodegradable, and/or water-soluble material. Also optionally in such embodiments the device diagnostic insert and/or housing is/are adapted to accept a test strip, including for example a nitrocellulose test strip. In related embodiments, kits are provided including a housing, diagnostic insert and one or more test strips. In certain embodiments, the test strip is a non-nitrocellulose test strip.

Though depicted as single layers, each of the housing top 20A, housing bottom 20B, and diagnostic insert 30 may be comprised of one or more individual layers of material.

Exemplary devices contemplated herein may permit sample to be applied to the sample pad when the diagnostic insert is in, optionally the extended and/or retracted positions.

Devices of the present disclosure also often eliminate the need for a plastic backing card traditionally used in test strips. Rather, the same non-synthetic matrix material used in other aspects or components is used to provide rigidity and/or a fluid barrier to the device. Often, a non-synthetic matrix material that is water dispersible or soluble is used as a backing material. In frequent embodiments, the non-synthetic matrix material used as a backing is coated with a material or agent with limited, slow, or delayed wettability. Often, the non-synthetic matrix material as a backing is a material with limited, slow, or delayed wettability. A second or other water dispersible or soluble material of increased rigidity versus the water dispersible or soluble matrix material, for example, is also frequently used. In certain embodiments, the device comprises two or more different water dispersible or soluble materials. In certain embodiments, the device comprises three or more different water materials. In certain embodiments the device comprises two of the same or similar water dispersible or soluble matrix materials and a second (e.g., different) water dispersible or soluble material sandwiched between the two same or similar water dispersible or soluble matrix materials. In such embodiments, the device is adapted to provide for the same or different assays on each of the two same or similar water dispersible or soluble matrix materials. Also, in such embodiments, each of the same or similar water dispersible or soluble matrix defines an individual flow path. Most frequently, when fluid enters one of the two individual flow-paths, or reaches a pre-determined location on the device, it does not pass through to the other of the two individual flow paths.

Devices of the present disclosure also often eliminate the need for a laminate or cover tape or polymer traditionally used in test strips, for example, either by substitution of a water-soluble and/or water dispersible or soluble coating, or in some instances, eliminating the need for such cover tape.

Devices of the present disclosure also often eliminate or forego the need or desire for a non-flushable plastic housing or cassette. In fact, the presence or use of non-flushable materials such as a plastic housing departs from a general theme of the present disclosure to provide for environmentally sensitive water-dispersible or soluble devices that permit a level of privacy not heretofore achievable. Plastic housings and non-flushable components such as test strips containing nitrocellulose must be disposed in solid waste containers. Moreover, plastic housings or cassettes prohibit discreet packaging of fully functional devices. In contrast, in many embodiments of the presently contemplated devices, the device itself is foldable to be stored in a small area. Usage merely entails unfolding and contacting a sample with the device.

In a frequent embodiment, the sample receiving zone accepts a fluid sample that may contain analytes of interest. In another embodiment, the sample receiving zone is dipped into a fluid sample. A label zone is located downstream of the sample receiving zone, and contains one or more mobile label reagents that recognize, or are capable of binding the analytes of interest. Further, a test region is disposed downstream from the label zone, and often contains test and control zones. The test zone(s) generally contain a reagent or adaptation that permits the restraint of a particular analyte of interest in each test zone. Frequently, the reagent or adaptation included in the test zone(s) comprises an immobilized capture reagent that binds to the analyte of interest. Generally the immobilized capture reagent specifically binds to the analyte of interest. Although, on occasion, the reagent or adaptation that permits the restraint of a particular analyte of interest in each test zone comprises another physical, chemical or immunological adaptation for specifically restraining an analyte of interest. Thus, as the fluid sample flows along the matrix, the analyte of interest will first bind with a mobilizable label reagent in the label zone, and then become restrained in the test zone. In occasional embodiments, the test region is comprised of a material that is opaque in a dry state and transparent in a moist state. Thus, when a control zone comprising a mark on the device is utilized, this mark is positioned about the test region such that it becomes visible within the test region when the test region is in a moist state.

Often, the fluid sample flows along a flow path running from the sample receiving zone (upstream), through the label zone, and then to the test and control zones (together comprised in a test region) (downstream). Optionally, the fluid sample may thereafter continue to an absorbent zone.

Exemplary devices may be operated as follows:
Scenario 1: Extend first, then use
1. Grab diagnostic insert tab at thumb gap
2. Pull diagnostic insert until fully extended
   a. Until diagnostic insert is stopped, internally
   b. Viewing window in housing top will be aligned with test area comprised in diagnostic insert when fully extended
4. Apply sample onto sample pad (e.g., midstream, pipette, or dipping)
5. Lay test down (e.g., flat) and allow to run
6. Read results in results window of housing top Scenario 2: Apply sample before extension
1. Apply sample to sample pad through results window opening in outer housing
2. Allow device to run
3. Grab diagnostic insert tab at thumb gap
4. Pull diagnostic insert tab until fully extended
   a. Until diagnostic insert is stopped, internally
   b. Viewing window in housing top will be aligned with test area comprised in diagnostic
5. Read results in results window In certain embodiments, the matrix material is a single, non-layered, material. In such embodiments, the matrix material has an increased thickness that is similarly treated via submersion, roll lamination or another method. Also in certain embodiments, multiple different matrix materials are laminated and bound together. In such embodiments, the different matrix materials can be separately laminated or laminated together via submersion, roll lamination or another method.

In certain embodiments, a treated matrix material is prepared, and after preparation holes (e.g., perforations as discussed herein) are introduced though the treated matrix material to enhance dissolution/dispersion and/or decrease sinking and dispersion timing. The holes can be introduced by any known means, including clean-cut and sealed-cut methods. A clean-cut refers to a cut such that the cut may be introduced through individual fibers, thus exposing the internal and untreated surfaces (i.e., surfaces not containing the coating/lamination solution) of the cut area to the environment. A sealed-cut refers to a cut such that the cut may be introduced through individual fibers, but the cut surface is sealed such that the internal surfaces of the fibers are not exposed to the environment, for example, since they are covered with the coating/lamination solution, heat-sealed, etc. Conventional cutting methods are contemplated, including mechanical cutting via die cutting or otherwise with a sharpened instrument in addition to heat-, light-, and/or chemical-based cutting methods. Debossing may also be employed, wherein patterns are introduced to the surface of the matrix material in certain areas (e.g., through a press or another method or means) to provide an aesthetic texture, decrease hydrophobicity by introducing a perforation or hole, and increase dispersion potential in the areas of the material that have been debossed.

The above examples are included for illustrative purposes only and are not intended to limit the scope of the disclosure. Many variations to those methods, systems, and devices described above are possible. Since modifications and variations to the examples described above will be apparent to those of skill in this art, it is intended that this invention be limited only by the scope of the appended claims.

One skilled in the art will appreciate further features and advantages of the presently disclosed methods, systems and devices based on the above-described embodiments. Accordingly, the presently disclosed methods, systems and devices are not to be limited by what has been particularly shown and described, except as indicated by the appended claims. All publications and references cited herein are expressly incorporated herein by reference in their entirety and/or for the specific reason for which they are cited herein.

We claim:

1. A diagnostic device for identifying or quantifying an analyte of interest in a biological sample, comprising:
a housing comprised of a housing top and a housing bottom;
a test strip; and
a diagnostic insert adapted to support the test strip,
wherein the housing includes a housing opening adapted to permit the diagnostic insert to be received within the housing in a translatable configuration,
wherein the diagnostic insert is configured to move between a retracted position and an extended position within the housing opening,
wherein the housing and the diagnostic insert are substantially flat, and the housing further comprises a window positioned in a top surface of the housing, wherein the window: (a) is covered by a material that is light translucent, and/or (b) provides optical and/or fluid access to the diagnostic insert,
wherein the housing top and the housing bottom each has a gap, the gap of the housing top and the gap of the housing bottom being aligned with each other to form a thumb gap, wherein the diagnostic insert in retracted position is exposed at the area corresponding to the thumb gap on the housing,
wherein the housing or the diagnostic insert are comprised of at least one water-dispersible, flushable, or water-soluble material, and
wherein each of the housing top, the housing bottom, and/or the diagnostic insert is comprised of a treated matrix material treated with a material or agent with limited, slow or delayed wettability, and wherein the treated matrix material is configured to include one or more perforations through the treated matrix material adapted to enhance dissolution or dispersion, and/or decrease sinking and dispersion timing.

2. The diagnostic device of claim 1, wherein the housing and the diagnostic insert are comprised of water-dispersible, flushable, or water-soluble material.

3. The diagnostic device of claim 1, wherein the retracted position of the diagnostic insert situates the majority or the entirety of the diagnostic insert within the housing; and the extended position of the diagnostic insert situates at least a portion of the diagnostic insert outside of the housing.

4. The diagnostic device of claim 3, further comprising a sample pad having a sample application surface positioned in the diagnostic insert,
wherein the sample pad is positioned in an opening in the diagnostic insert, and the diagnostic device further comprises a downstream portion integrated into or on top of the top surface of the diagnostic insert, and
wherein the downstream portion comprises a label zone, a control zone and/or a test zone; and
wherein the window: (a) is covered by the material that is light translucent, and/or (b) provides optical and/or fluid access to the diagnostic insert.

5. The diagnostic device of claim 3, further comprising a sample pad having a sample application surface positioned in the diagnostic insert,
wherein the sample pad is positioned in an opening in the diagnostic insert, and the diagnostic device further comprises a downstream portion integrated into or on top of the top surface of the diagnostic insert, and
wherein the downstream portion comprises a label zone, a control zone and/or a test zone; and
wherein the window is covered by a material that is at least partially translucent and must be opened or removed for a user to view a test result.

6. The diagnostic device of claim 1, wherein the diagnostic insert or the housing is adapted to removably receive the test strip.

7. The diagnostic device of claim 6, further comprising a sample pad having a sample application surface positioned in the diagnostic insert.

8. The diagnostic device of claim 7, wherein the sample pad is positioned in an opening in the diagnostic insert, and the diagnostic device further comprises a downstream portion integrated into or on top of the top surface of the diagnostic insert, and wherein the downstream portion comprises a label zone, a control zone and/or a test zone.

9. The diagnostic device of claim 1, wherein the test strip comprises a non-water-dispersible, non-flushable, or non-water-soluble material.

10. The diagnostic device of claim 9, wherein the test strip
(a) is comprised at least partially of nitrocellulose, or
(b) is comprised or consists of non-nitrocellulose material.

11. The diagnostic device of claim 1, wherein the test strip is a lateral flow test strip and comprises a water-dispersible, flushable, or water-soluble material.

12. The diagnostic device of claim 1, wherein the analyte of interest comprises a toxin, an organic compound, a protein, a peptide, a microorganism, a bacteria, a virus, an amino acid, a nucleic acid, a carbohydrate, a hormone, a steroid, a vitamin, a drug, a pollutant, a pesticide, an antigenic substance, a hapten, an antibody, and/or a metabolite of or an antibody to any of the foregoing.

13. The diagnostic device of claim 1, further comprising a sample pad having a sample application surface positioned in the diagnostic insert.

14. The diagnostic device of claim 13, wherein the sample pad is positioned in an opening in the diagnostic insert, and the diagnostic device further comprises a downstream portion integrated into or on top of the top surface of the diagnostic insert, and wherein the downstream portion comprises a label zone, a control zone and/or a test zone.

15. The diagnostic device of claim 1, wherein the diagnostic insert is rigid.

16. The diagnostic device of claim 1, wherein the window is covered by a material that is at least partially translucent and must be opened or removed for a user to view a test result.

* * * * *